United States Patent
Shirono

(10) Patent No.: US 11,061,148 B2
(45) Date of Patent: Jul. 13, 2021

(54) RADIATION IMAGING APPARATUS, RADIATION IMAGING METHOD, AND STORAGE MEDIUM

(71) Applicant: CANON KABUSHIKI KAISHA, Tokyo (JP)

(72) Inventor: Jumpei Shirono, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/524,845

(22) Filed: Jul. 29, 2019

(65) Prior Publication Data

US 2019/0346573 A1    Nov. 14, 2019

Related U.S. Application Data

(63) Continuation of application No. PCT/JP2017/044766, filed on Dec. 13, 2017.

(30) Foreign Application Priority Data

Feb. 1, 2017   (JP) .............................. JP2017-016976

(51) Int. Cl.
   *G01T 1/17* (2006.01)

(52) U.S. Cl.
   CPC ...................................... *G01T 1/17* (2013.01)

(58) Field of Classification Search
   CPC ............... G01T 1/17; G01T 1/36; A61B 6/00
   USPC ........................................................ 250/261
   See application file for complete search history.

(56) References Cited

U.S. PATENT DOCUMENTS

| 4,442,489 A * | 4/1984 | Wagner ................. A61B 6/032 378/19 |
| 2002/0146087 A1 * | 10/2002 | Izumi ....................... G01T 1/17 376/245 |
| 2004/0206909 A1 * | 10/2004 | Izumi ....................... G01T 1/17 250/395 |
| 2006/0126776 A1 * | 6/2006 | Izumi ....................... G01T 1/17 376/255 |
| 2009/0279665 A1 * | 11/2009 | Takahashi ............. A61B 6/542 378/62 |

(Continued)

FOREIGN PATENT DOCUMENTS

| JP | 2009285356 A | 12/2009 |
| JP | 2017083408 A | 5/2017 |

OTHER PUBLICATIONS

International Search Report dated Mar. 20, 2018 in corresponding International Patent Application No. PCT/JP2017/044766.

*Primary Examiner* — David P Porta
*Assistant Examiner* — Gisselle M Gutierrez
(74) *Attorney, Agent, or Firm* — Carter, DeLuca & Farrell LLP

(57) ABSTRACT

A radiation imaging apparatus comprises: a detecting unit configured to obtain measurement information that is based on the result of detection of radiation with which a subject has been irradiated; an obtaining unit configured to obtain an average energy of the radiation based on pieces of measurement information obtained through measurement of the radiation that has been performed a plurality of times; and a correction unit configured to correct the average energy based on a characteristic of the radiation with which the subject has been irradiated.

14 Claims, 13 Drawing Sheets

(56) References Cited

U.S. PATENT DOCUMENTS

| | | | |
|---|---|---|---|
| 2011/0147601 A1* | 6/2011 | Niekawa | A61B 6/4233 |
| | | | 250/370.09 |
| 2013/0022170 A1 | 1/2013 | Cho | |
| 2013/0068961 A1* | 3/2013 | Tajima | G01T 1/17 |
| | | | 250/394 |
| 2014/0284491 A1* | 9/2014 | Sato | G01T 1/247 |
| | | | 250/393 |
| 2016/0231436 A1* | 8/2016 | Tanaka | G01T 1/1606 |
| 2018/0011203 A1* | 1/2018 | Katayama | G01T 1/023 |
| 2018/0296170 A1 | 10/2018 | Shirono | |
| 2018/0296171 A1 | 10/2018 | Shirono | |
| 2019/0021680 A1 | 1/2019 | Shirono | |
| 2019/0235093 A1* | 8/2019 | Tanaka | H04N 5/32 |

\* cited by examiner

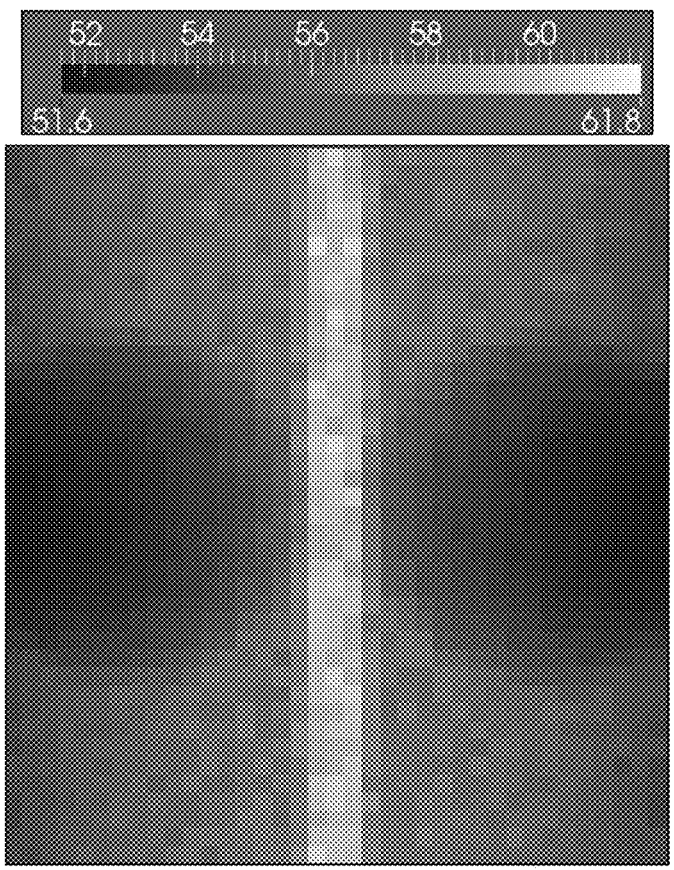
F I G. 14
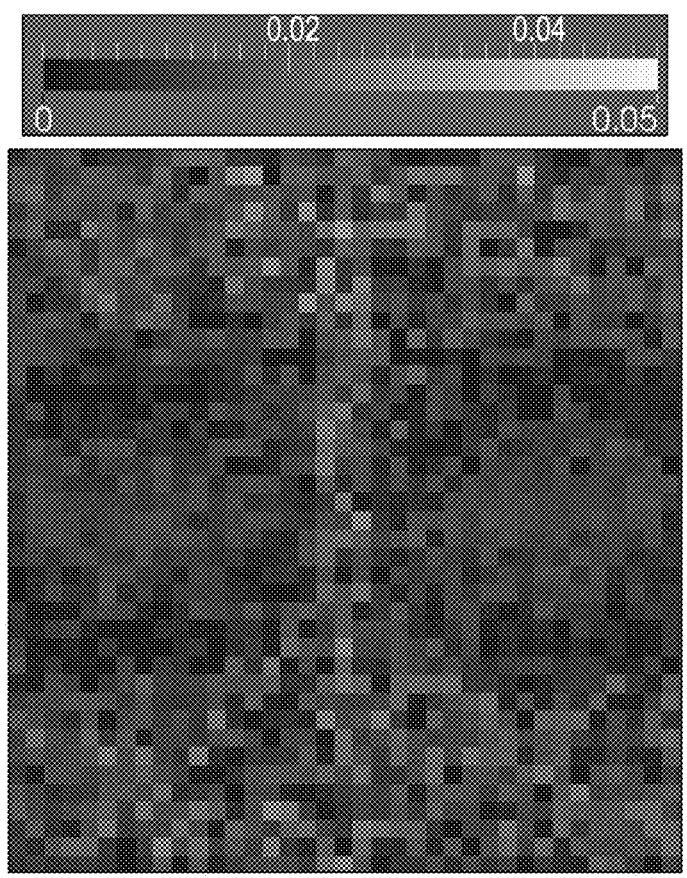
F I G. 15

RADIATION IMAGING APPARATUS, RADIATION IMAGING METHOD, AND STORAGE MEDIUM

CROSS-REFERENCE TO RELATED APPLICATIONS

This application is a Continuation of International Patent Application No. PCT/JP2017/044766, filed Dec. 13, 2017, which claims the benefit of Japanese Patent Application No. 2017-016976, filed Feb. 1, 2017, both of which are hereby incorporated by reference herein in their entirety.

BACKGROUND OF THE INVENTION

Field of the Invention

The present invention relates to a radiation imaging apparatus, a radiation imaging method, and a storage medium.

Background Art

A radiation detecting apparatus is an apparatus that renders internal structures of a subject as a grayscale image by measuring radiation that has passed through the subject, using a detector. When passing through a subject, radiation emitted from a radiation source is attenuated according to the type (e.g. fat, a bone, or a muscle) or the thickness of the part that radiation passes through. By measuring integrated values of the energy of radiation that has passed through a subject using a radiation detecting unit, and by forming a grayscale image based on the measurement values, it is possible to obtain a grayscale image that reflects internal structures of the subject.

PTL1 discloses technique for estimating internal structures that cannot be distinguished from each other when integrated values of energy are approximately the same, by utilizing moment information that has been obtained by performing measurement a plurality of times using the radiation detecting unit, and utilizing average energy of radiation that has entered the radiation detecting unit.

CITATION LIST

Patent Literature

PTL1: Japanese Patent Laid-Open No. 2009-285356

Generally, the energy of radiation that enters the radiation detecting unit has energy distribution, and there is a problem in that the average energy obtained through the method according to PTL1 includes an error due to the characteristics of radiation.

The present invention has been made in view of the above problem, and provides technique for reducing an error that occurs due to the characteristics of radiation, through correction, and making it possible to obtain average energy with high accuracy.

SUMMARY OF THE INVENTION

A radiation imaging apparatus according to one aspect of the present invention is a radiation imaging apparatus comprising: a detecting unit configured to obtain measurement information that is based on the result of detection of radiation with which a subject has been irradiated; an obtaining unit configured to obtain an average energy of the radiation based on pieces of measurement information obtained through measurement of the radiation that has been performed a plurality of times; and a correction unit configured to correct the average energy based on a characteristic of the radiation with which the subject has been irradiated.

Further features of the present invention will become apparent from the following description of exemplary embodiments with reference to the attached drawings.

BRIEF DESCRIPTION OF THE DRAWINGS

The attached drawings are included in DESCRIPTION, constitute a part of DESCRIPTION, show embodiments of the present invention, and are used together with descriptions of the embodiments to illustrate the principles of the present invention.

FIG. 14 is a diagram showing an example of a corrected average energy image.

FIG. 15 is a diagram showing an example of a relative error image regarding corrected average energy.

DESCRIPTION OF THE EMBODIMENTS

The following describes embodiments of the present invention in an illustrative manner with reference to the drawings. Note that the constituent elements described in the embodiments are merely examples. The technical scope of the present invention is determined by CLAIMS, and not by the individual embodiments below.

First Embodiment

Figure 1:
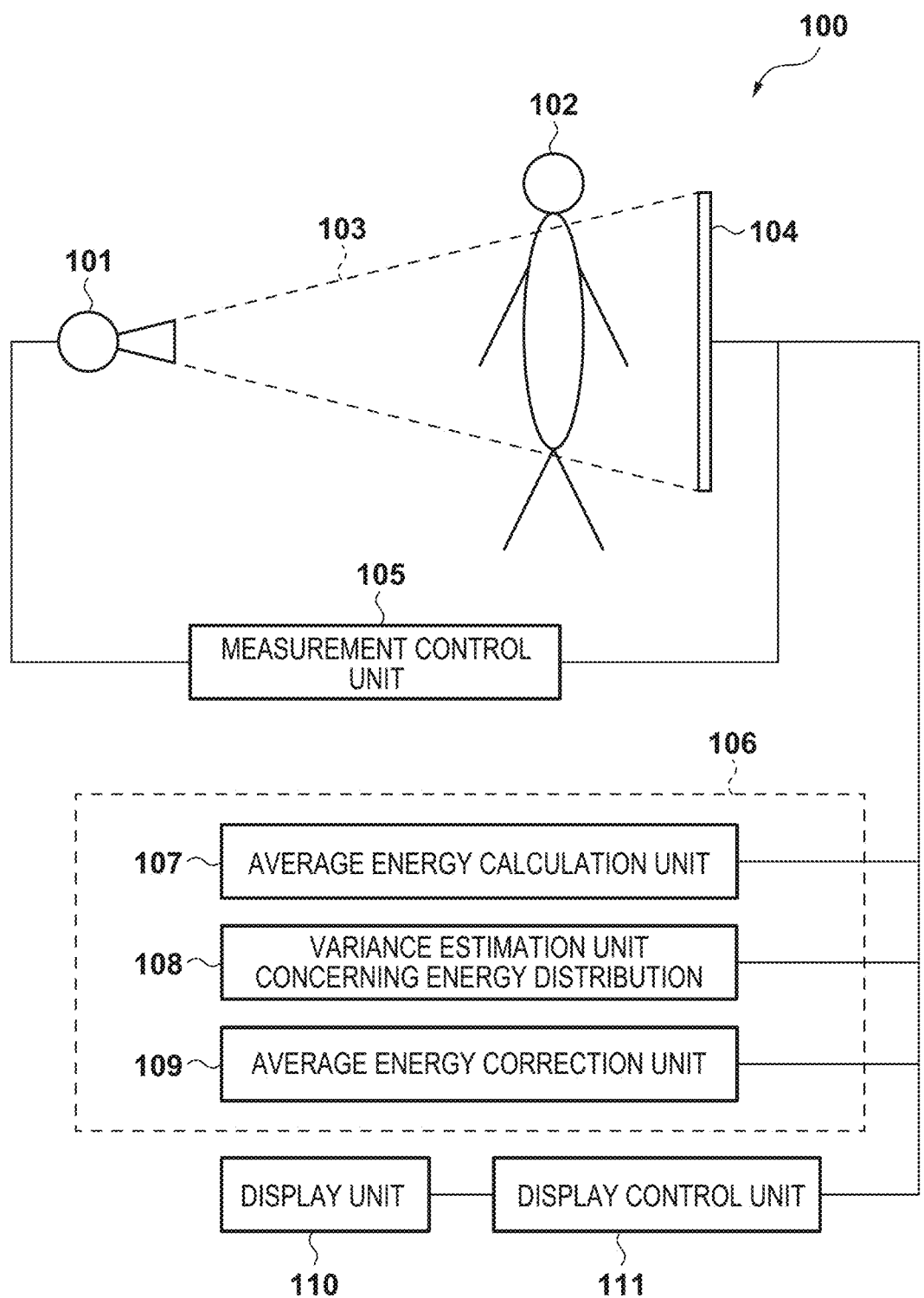
FIG. 1 is a schematic diagram showing a configuration of a radiation imaging apparatus according to a first embodiment.
Figure 2:
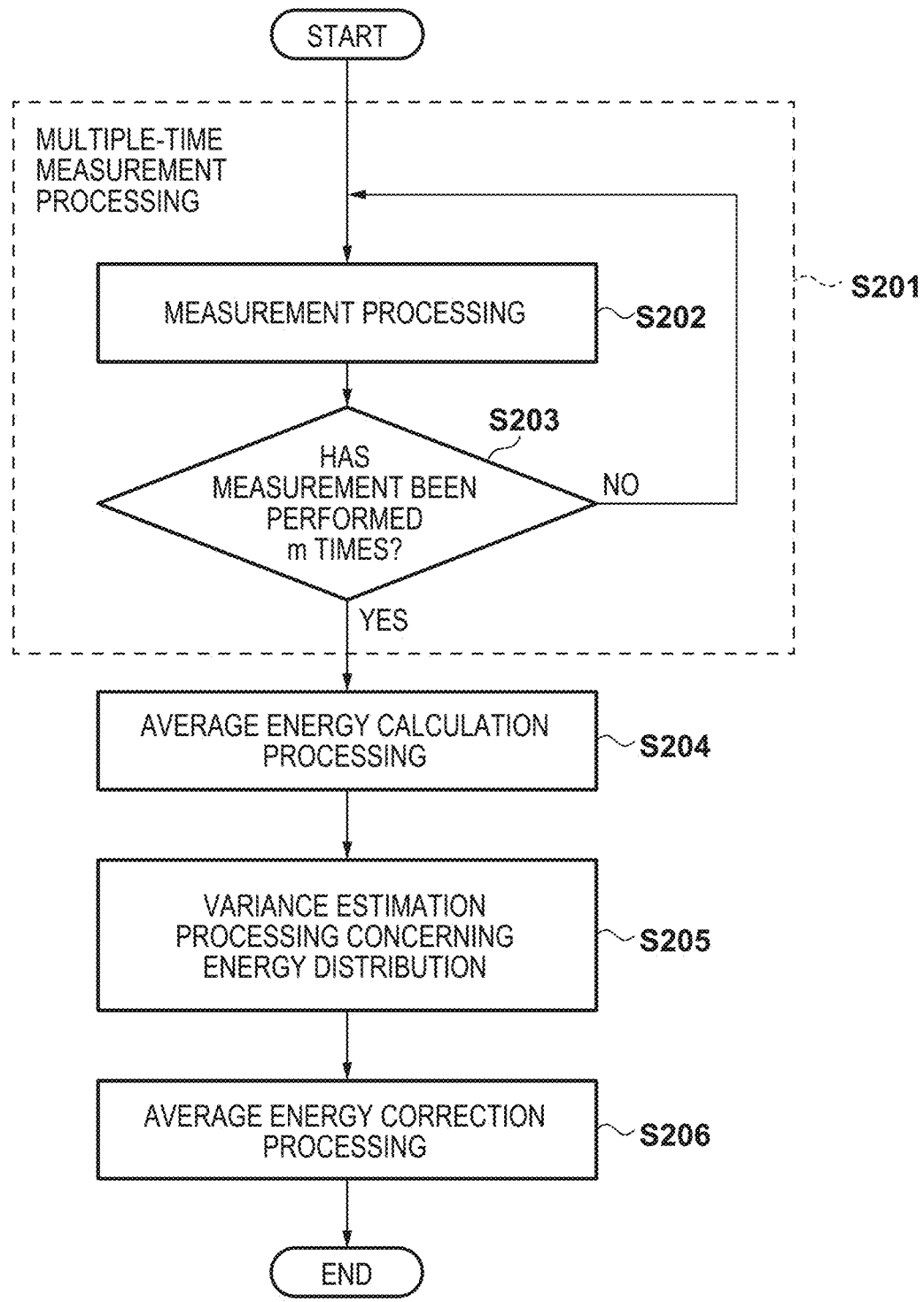
FIG. 2 is a flowchart for average energy correction processing according to the first embodiment.

The following specifically describes a first embodiment of the present invention with reference to the accompanying drawings. FIG. 1 is a schematic diagram showing a configuration of a radiation imaging apparatus according to the first embodiment, and FIG. 2 is a flowchart for average energy correction processing.

As shown in FIG. 1, a radiation imaging apparatus 100 includes a radiation generating unit 101, a radiation detecting unit 104, and an image processing unit 106. Although radiation in the present embodiment is an X ray, it may be an α ray, a β ray, a γ ray, or heavy particles. The reference numeral 103 indicates radiation emitted from the radiation generating unit 101, and the radiation detecting unit 104 outputs measurement information that is approximately proportional to the sum of energy of the radiation 103 that has entered the radiation detecting unit 104 during a certain period of time. In the present embodiment, the radiation detecting unit 104 has a plurality of detecting parts (detecting elements) that are two-dimensionally arranged. The configuration of a flat panel detector (FPD) in which a plurality of detecting elements are arranged in a grid pattern or the configuration of a line sensor may be employed as the radiation detecting unit 104. There may be only one detecting part (detecting element). The radiation detecting unit 104 obtains measurement information that is based on the result of detection of radiation with which a subject has been irradiated.

A measurement control unit 105 causes the radiation generating unit 101 that emits radiation, and the radiation detecting unit 104, to operate in conjunction with each other to control measurement of the energy of radiation. Specifically, in the present embodiment, the measurement control unit 105 controls measurement of the energy of radiation, which is performed a plurality of times, in a state where the subject is present between the radiation generating unit 101 and the radiation detecting unit 104. Although the present embodiment shows an example in which control is performed using a computer, the measurement control unit 105 may be formed using an integrated circuit or the like if similar functions can be achieved, and is not limited to any mode.

The radiation detecting unit 104 obtains measurement information that is based on the result of detection of radiation with which a subject has been irradiated. The radiation detecting unit 104 obtains the strength (energy) of radiation that has been output from the radiation generating unit 101 and has passed through a subject 102, using detecting parts (detecting elements). Specifically, the radiation detecting unit 104 obtains and outputs measurement information that is approximately proportional to the sum of energy of radiation that has entered one pixel of the detecting units (detecting elements) during a certain period of time. Although the subject 102 is a living organism in the present embodiment, an object other than a living organism, such as an industrial product, may be employed as the subject.

Measurement information obtained through measurement that has been performed by the radiation detecting unit 104 is transmitted to, and is processed by, the image processing unit 106. The image processing unit 106 includes an average energy calculation unit 107, a variance estimation unit 108 concerning energy distribution, and an average energy correction unit 109 as functional elements. In the present embodiment, processing that is performed by the image processing unit 106 is executed by a computer. The functions of the units included in the image processing unit 106 are achieved using a CPU, a GPU, and programs that are read out from a memory, for example (not shown). That is to say, processing that is performed by the average energy calculation unit 107, the variance estimation unit 108, and the average energy correction unit 109 is realized by a computer executing functions of programs corresponding to the functional elements. The image processing unit 106 may be formed using an integrated circuit or the like if similar functions can be achieved, and is not limited to any mode.

A display unit 110 is a liquid crystal display or a CRT, for example, or a display unit of any other type that is viewable for humans. The display unit 110 displays results obtained by the radiation detecting unit 104 and the image processing unit 106 included in the radiation detecting apparatus according to the present embodiment. A display control unit 111 controls display on the display unit 110. For example, the display control unit 111 can display an image showing the distribution of average energy corrected by the average energy correction unit 109, and an image showing the distribution of uncorrected average energy, on the display unit 110.

Next, procedures for average energy correction processing that is performed by the radiation imaging apparatus 100 according to the first embodiment will be described with reference to the flowchart shown in FIG. 2.

Multiple-time Measurement Processing (S201)

First, in step S201, the measurement control unit 105 executes multiple-time measurement processing. The measurement control unit 105 causes the radiation generating unit 101 and the radiation detecting unit 104 to operate in conjunction with each other to execute multiple-time measurement processing. The multiple-time measurement processing S201 includes two steps, namely steps S202 and S203. In step S202, measurement is performed. The measurement control unit 105 controls the radiation generating unit 101 so that radiation is emitted therefrom under a constant tube voltage, and causes the radiation detecting unit 104 to output the results of detection of the radiation that has entered the detecting elements thereof, at constant intervals. Measurement information obtained through measurement performed by the detecting elements of the radiation detecting unit 104 is denoted as $d_i$. The index i indicates that the measurement information was obtained at the $i^{th}$ measurement.

In step S203, the measurement control unit 105 determines whether or not measurement has been completed a predetermined number of times (m is a natural number no less than 2). If measurement has not been completed the predetermined number of times (m times) (S203—No), processing returns to step S201, and measurement is performed again. On the other hand, at determination in step S203, if measurement has been completed the predetermined number of times (m times) (S203—Yes), processing proceeds to step S204. As a result of measurement being performed the predetermined number of times (m times), pieces of measurement information corresponding to m times are input to the average energy calculation unit 107.

Average Energy Calculation Processing: S204

In step S204, the average energy calculation unit 107 obtain the average energy of radiation based on the pieces of measurement information obtained through measurement of radiation that has been performed a plurality of times. Specifically, the average energy calculation unit 107 obtains uncorrected average energy $E_{stat}$ through an expression (1) based on the moment of pieces of measurement information obtained through measurement of radiation that has been performed a plurality of times.

[Math. 1]

$$E_{stat} = \frac{V}{M} \quad (1)$$

Here, M denotes a first-order moment about the origin for d, and V denotes a second-order central moment for d, which are specifically calculated as shown in (2).

[Math. 2]

$$M = \frac{1}{m}\sum_{i=1}^{m} d_i, \, V = \frac{1}{m-1}\sum_{i=1}^{m}(d_i - M)^2 \quad (2)$$

In the calculations in (1) and (2), multiplication by a conversion coefficient for conversion between measurement information and energy may be employed. Although some of the calculations in the following description may require a conversion coefficient, such a conversion coefficient is omitted herein in order to simplify the descriptions thereof. Also, in the calculation of V, division by m (the number of measurements) may be performed instead of that by m−1.

Variance Estimation Processing concerning Energy Distribution: S205

Figure 3:
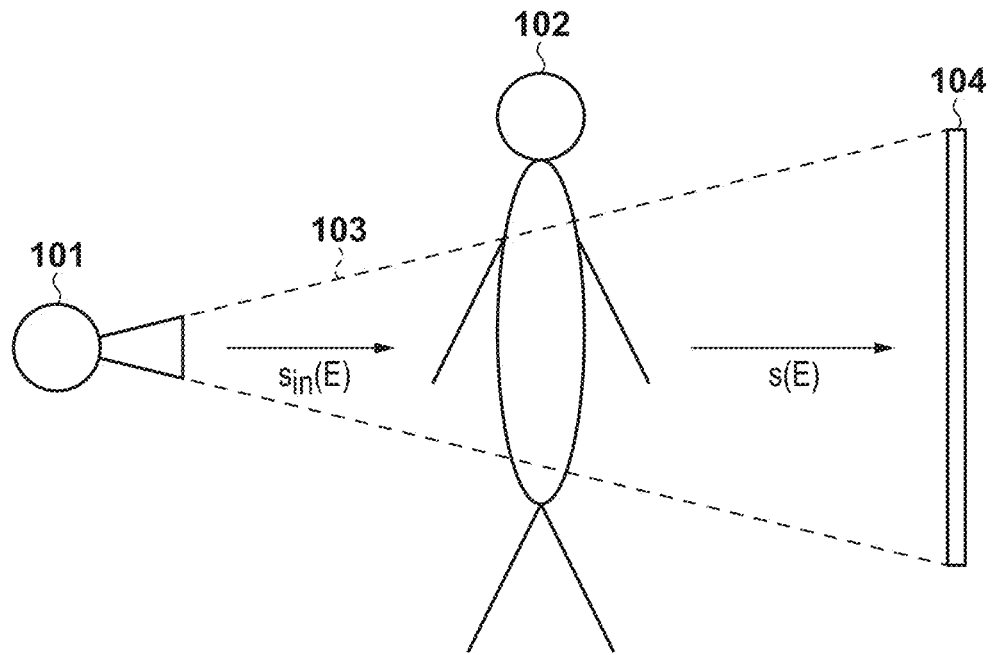
FIG. 3 is a diagram showing a state where radiation passes through a subject and enters a radiation detecting unit.
Figure 4:
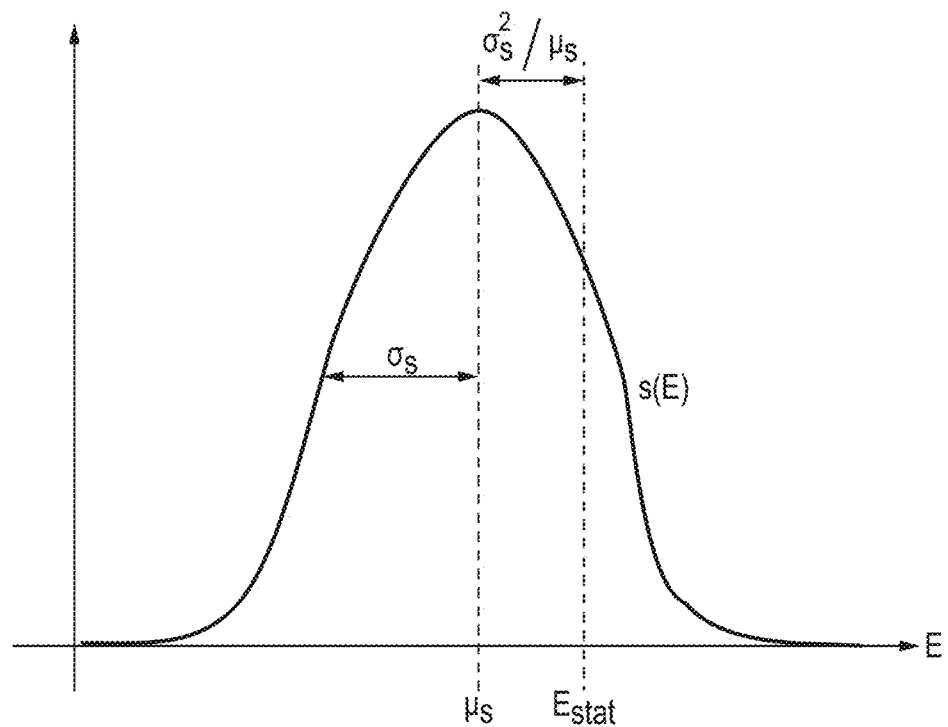
FIG. 4 is a schematic diagram for the energy distribution of radiation that has entered the radiation detecting unit.

Next, in step S205, the variance estimation unit 108 concerning energy distribution estimates the variance of the energy distribution of radiation as a characteristic of the radiation detected by the radiation detecting unit 104. FIG. 3 is a diagram showing a state where the radiation 103 emitted from the radiation generating unit 101 passes through the subject 102 and enters the radiation detecting unit 104, and FIG. 4 is a schematic diagram showing the energy distribution of radiation that has entered the radiation detecting unit 104. The radiation 103 emitted from the radiation generating unit 101 has an energy distribution that varies depending on a tube voltage, a filter, and so on. The energy distribution (the probability density function) of radiation that has not passed through the subject 102 is denoted as $s_{in}(E)$. Here, E denotes the energy of radiation. The energy distribution of radiation changes while the radiation passes through the subject 102, and the radiation thereafter enters the radiation detecting unit 104. The energy distribution (the probability density function) of radiation that has been detected by the radiation detecting unit 104, which is the energy distribution of radiation that has passed through the subject 102, is denoted as s(E).

The horizontal axis in FIG. 4 indicates the energy of radiation, and the curved line in the figure indicates s(E), which is the energy distribution (the probability density function) of the radiation detected by the radiation detecting unit 104. The variance $\sigma_s^2$ of the energy distribution s(E) of radiation is estimated through this processing. The variance $\sigma_s^2$ of the energy distribution s(E) of radiation is indicated by an expression (3) shown below. In the expression (3), $\mu_s$ denotes a true average energy. FIG. 4 shows the true average energy $\mu_s$ and a standard deviation $\sigma_s$.

[Math. 3]

$$\sigma_s^2 = \int (E-\mu_s)^2 s(E)dE, \mu_s = \int Es(E)dE \quad (3)$$

The variance estimation unit 108 concerning energy distribution can use, as the variance of energy distribution, the variance of the energy distribution of radiation that has not passed through the subject. In processing that is performed to estimate the variance $\sigma_s^2$ of the energy distribution s(E) of radiation, the variance estimation unit 108 concerning energy distribution uses, as $\sigma_s^2$, the variance $\sigma_{sin}^2$ of the energy distribution (the probability density function) $s_{in}(E)$ of radiation that has not passed through the subject 102. If conditions for measurement are determined, $s_{in}(E)$ is determined independent of the subject 102. Therefore, measurement can be performed in a state where the subject is not present, using a spectrometer. Also, if $s_{in}(E)$ is known, the variance estimation unit 108 concerning energy distribution can obtain $\sigma_{sin}^2$ using the definition shown by the expression (3).

Average Energy Correction Processing: S206

Next, in step S206, the average energy correction unit 109 corrects the average energy based on the characteristics of the radiation with which the subject has been irradiated. Specifically, the average energy correction unit 109 corrects the average energy of the radiation based on the variance of the energy distribution of the radiation with which the subject has been irradiated. Here, as shown in an expression (4), the average energy correction unit 109 calculates a corrected average energy $E'_{stat}$, using $\sigma_s^2$ estimated in the variance estimation processing (S205) concerning energy distribution.

[Math. 4]

$$E'_{stat} = \frac{E_{stat} + \sqrt{E_{stat}^2 - 4\sigma_s^2}}{2} \quad (4)$$

In average energy calculation processing in step S204, the uncorrected average energy $E_{stat}$ obtained through the expression (1) does not match the true average energy $\mu_s$. Therefore, the average energy correction unit 109 performs processing to correct the average energy $E_{stat}$. Generally, when a radiation has a spectral distribution, the uncorrected average energy $E_{stat}$ is shifted from the true average energy $\mu_s$ by $\sigma_s^2/\mu_s$ as shown in FIG. 4. That is to say, (5) is satisfied.

[Math. 5]

$$E_{stat} = \mu_s + \frac{\sigma_s^2}{\mu_s} \quad (5)$$

Here, the true average energy $\mu_s$ is to be ultimately calculated. The expression (5) is an equation in terms of $\mu_s$ and $\sigma_s^2$, if $E_{stat}$ and $\sigma_s^2$ can be obtained, the average energy correction unit 109 can calculate the true average energy $\mu_s$. Here, the uncorrected average energy $E_{stat}$ can be obtained through the expression (1), and the variance $\sigma_s^2$ of the energy distribution of radiation can be obtained through the variance estimation processing S205 concerning energy distribution. By performing a numerical analysis on the equation, using the average energy $E_{stat}$ and the variance $\sigma_s^2$ of the energy distribution of radiation, the average energy correction unit 109 can obtain the true average energy $\mu_s$ as the corrected average energy.

Thus, average energy correction processing is complete. Also, if necessary, it is possible to display the average energy, the variance of the energy distribution of radiation, the true average energy (the corrected average energy), and so on, using the display unit 110, to check the effect of correction, or use them to make a diagnosis.

Next, an example in which the average energy is corrected through the above-described procedures will be described. In the following example, measurement data is created by performing a virtual imaging experiment through numerical calculation, and average energy correction processing is executed according to the above-described procedures.

Figure 5:
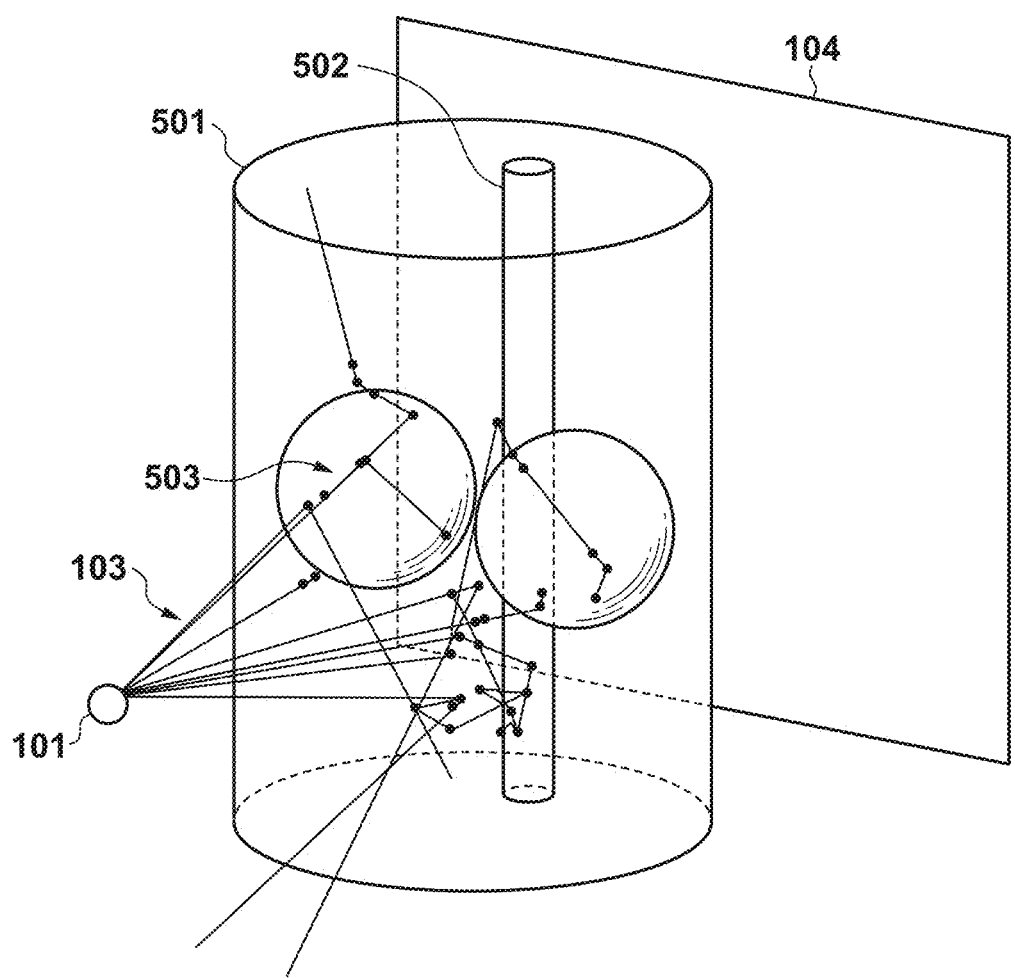
FIG. 5 is a diagram showing an example of an arrangement of subjects.

Geant4 (http://geant4.cern.ch/), which is software for simulating complex behaviors and reactions that elementary particles cause in materials, is used in average energy correction processing as software for numerical calculation. FIG. 5 is a diagram showing an example of the arrangement of subjects in the example. The subjects are models of living organisms, and the reference numeral 501 indicates a trunk, the reference numeral 502 indicates a bone, and the reference numeral 503 indicates a lung. In the example of arrangement shown in FIG. 5, the radiation generating unit 101 generates radiation that has energy distribution corresponding to a tube voltage of 80 kV. The subjects are arranged such that the radiation 103 is emitted from the radiation generating unit 101, and is detected by the radiation detecting unit 104.

Figure 6:
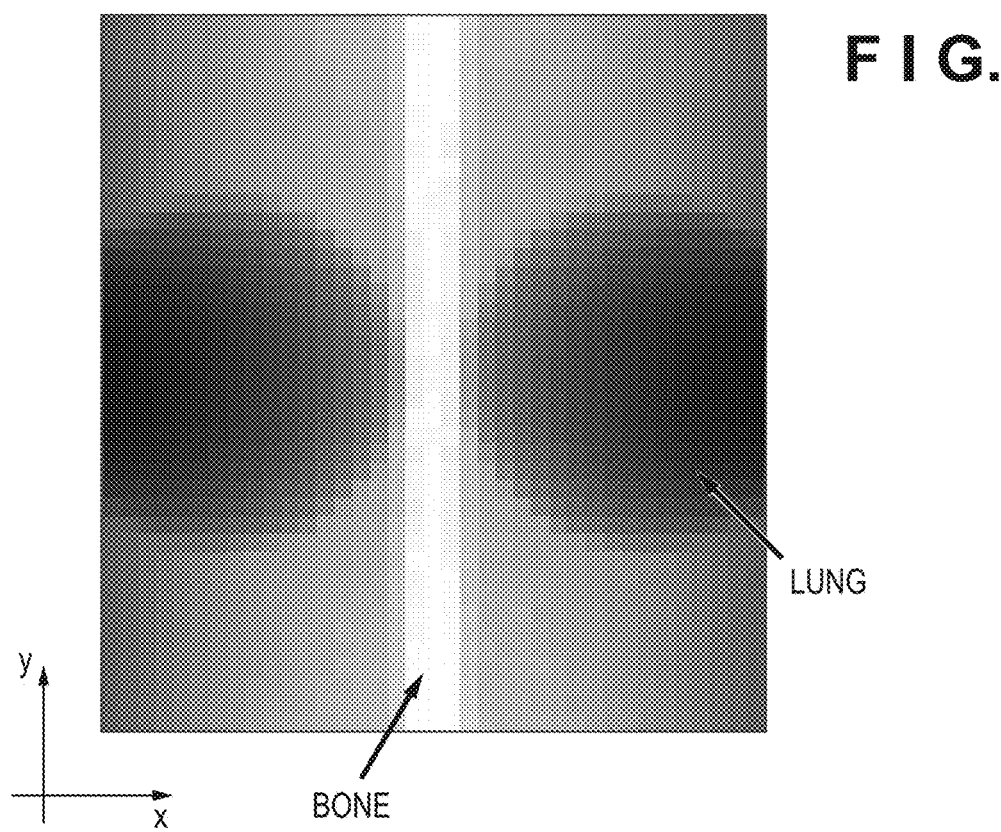
FIG. 6 is a diagram illustrating an image that is based on information detected by the radiation detecting unit.

FIG. 6 is a diagram showing an example of an image that is based on information that has been detected by the radiation detecting unit 104. The radiation detecting unit 104 is entirely hidden behind the trunk. The thickness of the trunk is large at the center in the x-axis direction, and the thickness decreases toward the ends in the x-axis direction. The captured image also shows such gradation. It can also be seen that the image shows the shadow of the bone, which extends in the y-axis direction in a central area in the x-axis direction. It can also be seen that the image shows the shadows of the lungs, which are present in a central area in the y-axis direction, respectively on two sides in the x-axis direction, and have a substantially spherical shape.

Figure 7:
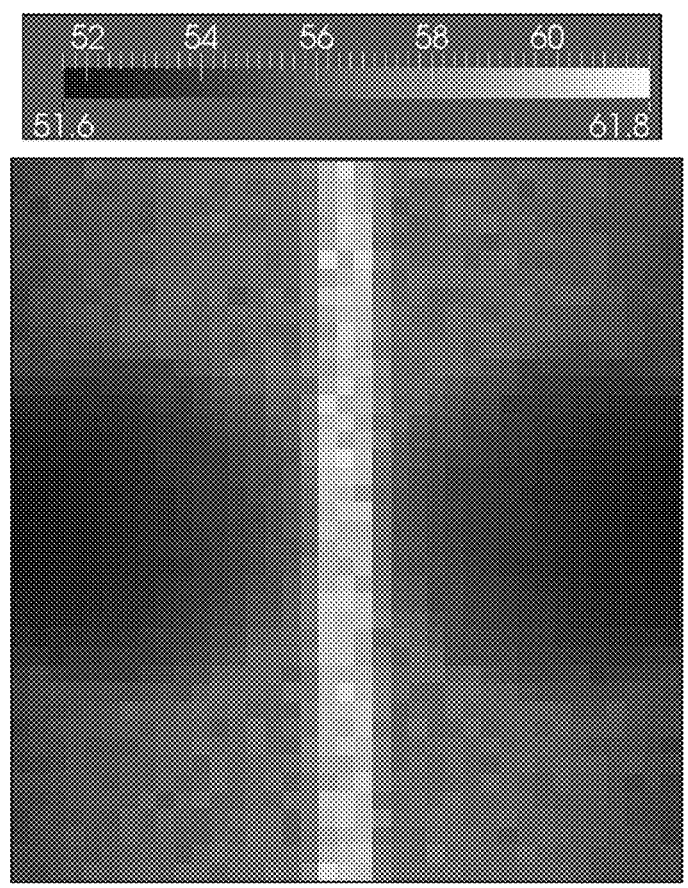
FIG. 7 is a diagram showing an example of a true average energy image.

FIG. 7 shows an image of the true average energy $\mu_s$, and the image in FIG. 7 is a correct image that is to be obtained. The scale shown above the image in FIG. 7 indicates a correspondence relationship between gray levels in the image and energy levels. The same applies to FIGS. 8 and 9, and the scale shown above each image indicates a correspondence relationship between gray levels in the image and energy levels.

Figure 8:
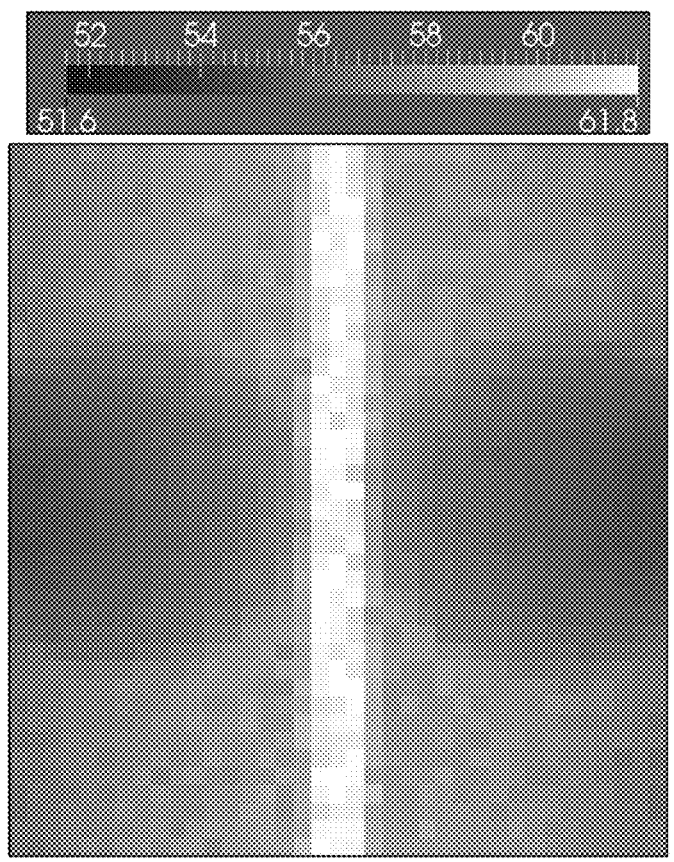
FIG. 8 is a diagram showing an example of an uncorrected average energy image.

FIG. 8 shows an image of the uncorrected average energy $E_{stat}$. When the image of the average energy $E_{stat}$ in FIG. 8 and the image of the true average energy in FIG. 7 are compared with each other, the image of the average energy $E_{stat}$ in FIG. 8 is whiter overall than the image of the true average energy in FIG. 7, which indicates that the average energy $E_{stat}$ has greater values than the true average energy $\mu_s$ and contains errors.

Figure 9:
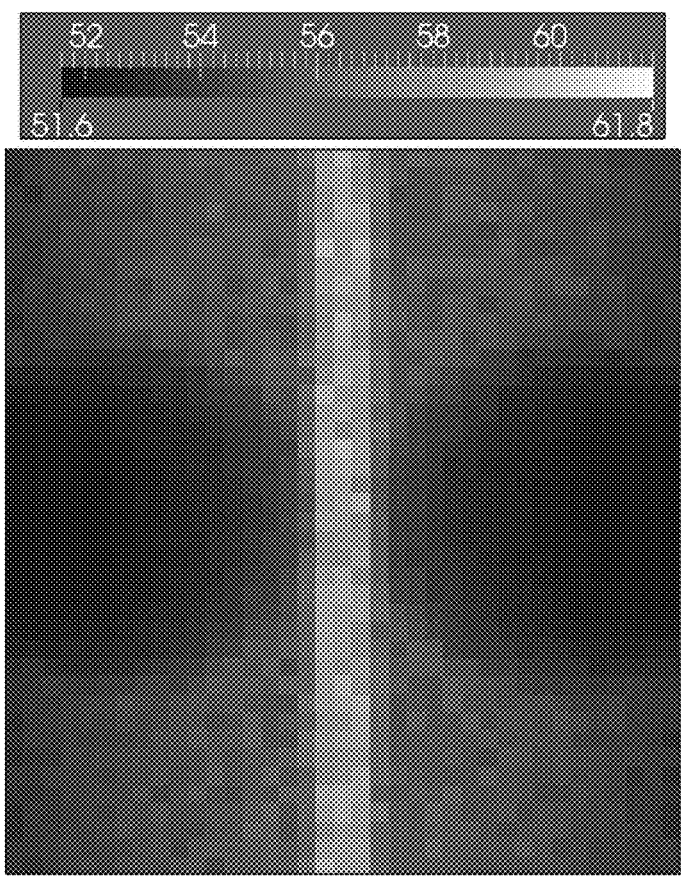
FIG. 9 is a diagram showing an example of a corrected average energy image.

FIG. 9 shows an image of the average energy $E'_{stat}$ corrected based on the processing procedures described with reference to FIG. 2. When the image of the corrected average energy $E'_{stat}$ in FIG. 9 and the image of the average energy $E_{stat}$ in FIG. 8 are compared with each other, the image of the corrected average energy $E'_{stat}$ in FIG. 9 is blacker overall than the image of the uncorrected average energy $E_{stat}$ (FIG. 8), which indicates that the values of the corrected average energy $E'_{stat}$ are close to the values of the true average energy $\mu_s$.

Figure 10:
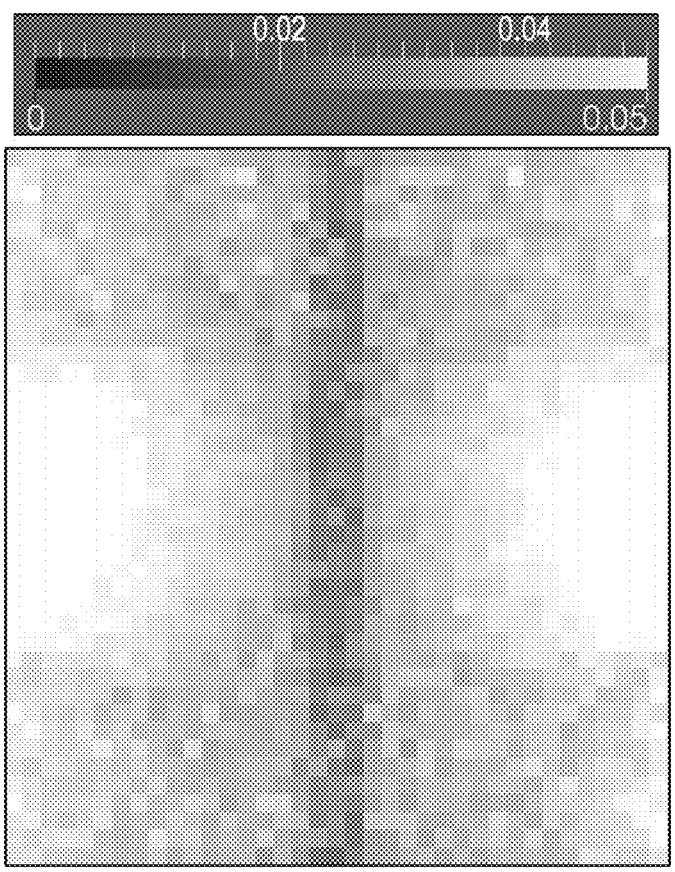
FIG. 10 is a diagram showing an example of a relative error image regarding uncorrected average energy.
Figure 11:
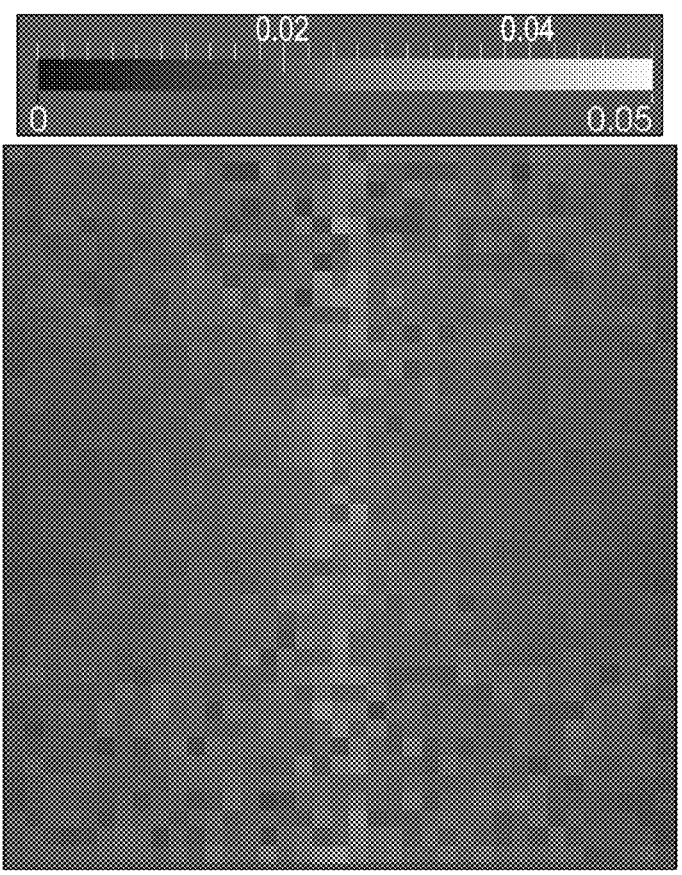
FIG. 11 is a diagram showing an example of a relative error image regarding corrected average energy.

In order to more easily make a comparison, FIG. 10 shows an image of relative errors between the uncorrected average energy $E_{stat}$ and the true average energy $\mu_s$, and FIG. 11 shows an image of relative errors between the corrected average energy $E'_{stat}$ and the true average energy $\mu_s$. The scale shown above each of the images in FIGS. 10 and 11 shows a correspondence relationship between gray levels in the image and relative errors of the energy levels. The density of the image decreases (the image becomes whiter) as the relative errors increase, and the density of the image increases (the image becomes blacker) as the relative errors decrease. When the images of relative errors in FIGS. 10 and 11 are compared with each other, the image of relative errors in the corrected average energy $E'_{stat}$ in FIG. 11 is blacker overall than the image of relative errors in the average energy $E_{stat}$ in FIG. 10, which indicates that the values of the corrected average energy $E'_{stat}$ are close to the values of the true average energy $\mu_s$, and the relative errors therein are smaller.

As described above, with the present embodiment, it is possible to calculate an average energy with high accuracy, through average energy correction processing. As a result, it is possible to accurately distinguish between internal structures that cannot be distinguished from each other if integrated values of energy are used. Although the variance of the energy distribution of radiation is used as a characteristic of the radiation in the present embodiment, a characteristic other than the variance of the energy distribution of radiation may be used. For example, a value indicating the variation (the dispersion) of the energy distribution of radiation, such as a value indicating the standard deviation or average deviation thereof, may be used instead.

Second Embodiment

Figure 12:
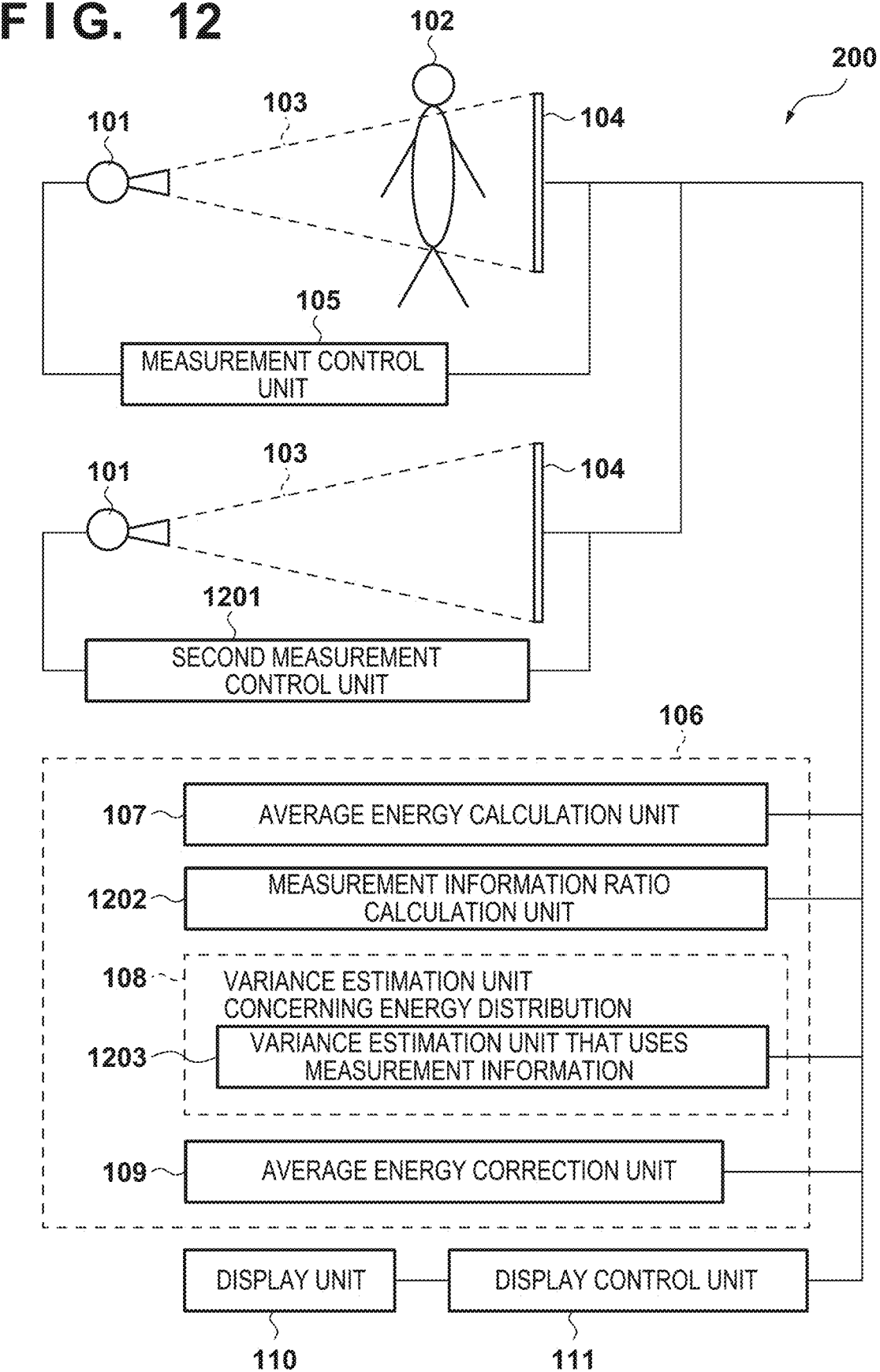
FIG. 12 is a schematic diagram showing a configuration of a radiation imaging apparatus according to a second embodiment.
Figure 13:
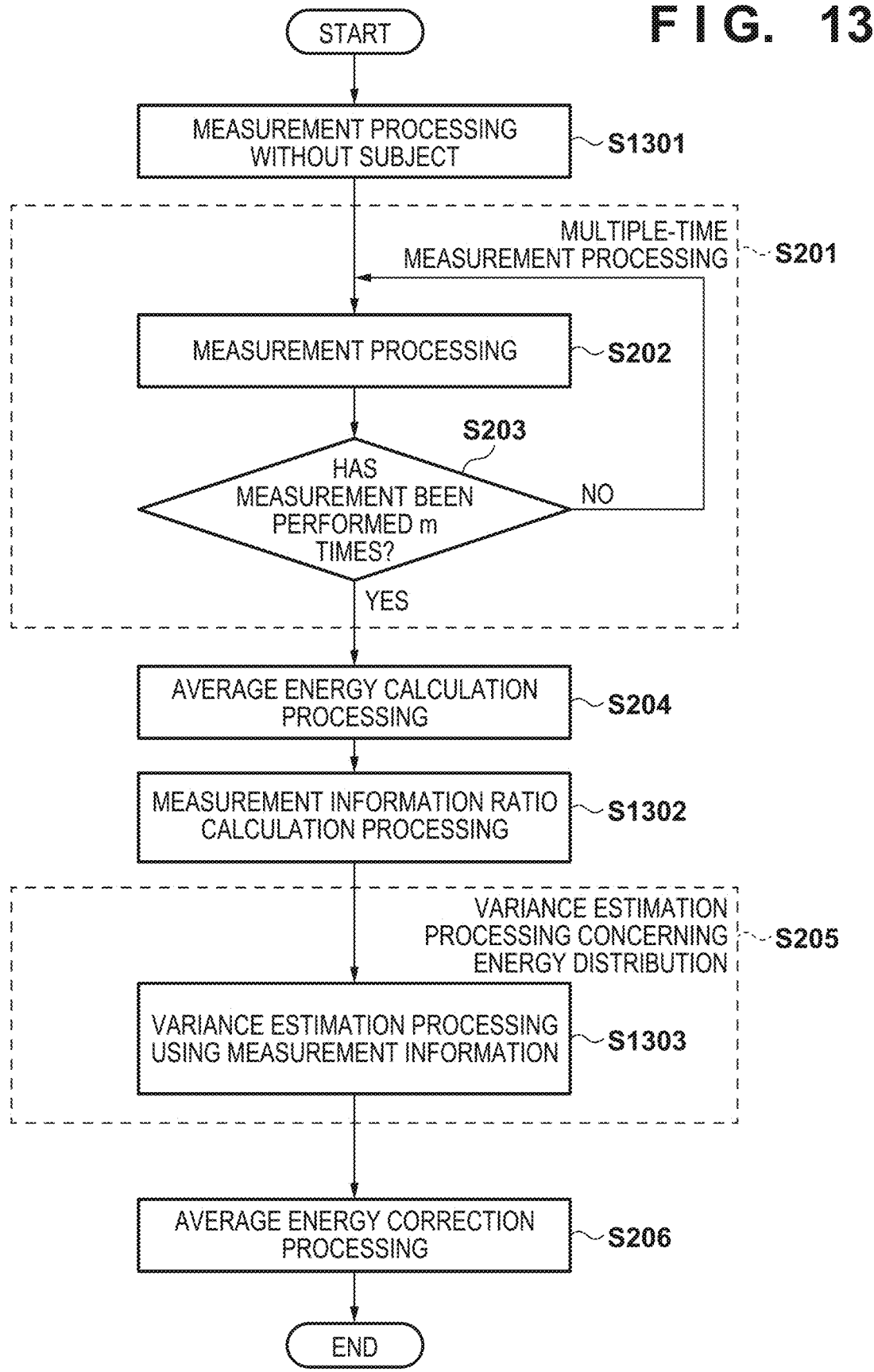
FIG. 13 is a flowchart for average energy correction processing according to the second embodiment.

The following specifically describes a second embodiment of the present invention with reference to the accompanying drawings. FIG. 12 is a diagram showing a configuration of a radiation imaging apparatus 200 according to the second embodiment, and FIG. 13 is a flowchart for an average energy correction processing. With reference to these figures, the following describes the configuration of the radiation imaging apparatus 200 and processing procedures according to the second embodiment. In order to avoid duplicative descriptions, the following describe parts that differ from the configuration according to the first embodiment. Parts that are assigned the same reference numerals perform the same functions and the same processing.

The radiation imaging apparatus 200 includes a second measurement control unit 1201. The second measurement control unit 1201 causes the radiation generating unit 101 and the radiation detecting unit 104 to operate in conjunction with each other to control measurement of the energy of radiation, in a state where the subject 102 is not present between the radiation generating unit 101 and the radiation detecting unit 104. In FIG. 12, in order to simplify descriptions, different functional elements are used when the subject is present and when the subject is not present. However, it is possible to perform control such that measurement is performed using the measurement control unit 105 described in the first embodiment in a state where the subject 102 is present between the radiation generating unit 101 and the radiation detecting unit 104, and measurement is further performed in a state where the subject 102 is not present. The second measurement control unit 1201 or the measurement control unit 105 control measurement of the energy of radiation in a state where the subject is not present between the radiation generating unit 101 and the radiation detecting unit 104.

The image processing unit 106 includes a ratio calculation unit 1202 and a variance estimation unit 1203 that uses measurement information, as functional elements of the image processing unit 106.

The ratio calculation unit 1202 calculates a ratio between pieces of measurement information. Specifically, the ratio calculation unit 1202 calculates a ratio between pieces of measurement information based on pieces of measurement information obtained through measurement of the energy of radiation that has been performed a plurality of times in a state where the subject is present, and measurement information obtained through measurement of the energy of radiation that has been performed in a state where the subject is not present. That is to say, the ratio calculation unit 1202 calculates a ratio between: pieces of measurement information obtained through measurement that has been performed a plurality of times under measurement control performed by the measurement control unit 105 in a state where the subject 102 is present; and measurement information obtained through measurement performed under measurement control performed by the second measurement control unit 1201 (or the measurement control unit 105), in a state where the subject 102 is not present. The ratio calculation unit 1202 can obtain a ratio between pieces of measurement information based on information regarding the material that constitutes the subject (e.g. an attenuation coefficient and information regarding the thickness and length of the constituent material), and the energy distribution of radiation in a state where the subject is not present. The variance estimation unit 108 can obtain the variance of the energy distribution of radiation based on the ratio between pieces of measurement information.

The variance estimation unit 1203 that uses measurement information estimates the variance of the energy of radiation based on the measurement information obtained through measurement control performed by the measurement control unit 105 and the second measurement control unit 1201. In the present embodiment, the variance estimation unit 1203 that uses measurement information, which is a constituent element of the variance estimation unit 108 concerning energy distribution, is used to estimate the variance of radiation energy.

The functions of the second measurement control unit 1201, the ratio calculation unit 1202, and the variance estimation unit 1203 are achieved using a CPU, a GPU, and programs that are read out from a memory, for example (not shown). That is to say, processing that is performed by the second measurement control unit 1201, the ratio calculation unit 1202, and the variance estimation unit 1203 is realized by a computer executing functions of programs corresponding to the functional elements. The image processing unit 106 may be formed using an integrated circuit or the like if similar functions can be achieved, and is not limited to any mode.

Next, procedures for average energy correction processing that is performed by the radiation imaging apparatus 200 according to the second embodiment will be described with reference to the flowchart shown in FIG. 13. The following describes processing that differs from the flowchart in FIG. 2, while duplicative descriptions are omitted.

Measurement Processing without Subject: S1301

First, in step S1301, the second measurement control unit 1201 (or the measurement control unit 105) causes the radiation generating unit 101 and the radiation detecting unit 104 to operate in conjunction with each other to control measurement of the energy of radiation in a state where the subject 102 is not present between the radiation generating unit 101 and the radiation detecting unit 104, thereby obtaining measurement information in a state where the subject is not present. In the measurement performed in step S1301, it is preferable that measurement conditions are the same as those in the multiple-time measurement processing (S201) described with reference to FIG. 2, except that the subject 102 is not present between the radiation generating unit 101 and the radiation detecting unit 104.

Multiple-time measurement processing is performed in steps S201 to S203, and average energy calculation processing is performed in step S204. In step S1301 and steps S201 to S203, the measurement control unit 105 and the second measurement control unit 1201 controls the radiation generating unit 101 such that the amount of radiation that is emitted from the radiation generating unit 101 is approximately constant.

Measurement Information Ratio Calculation Processing: S1302

Thereafter, in step S1302, the ratio calculation unit 1202 calculates a ratio r between: pieces of measurement information obtained through measurement that has been performed a plurality of times under measurement control performed by the measurement control unit 105 in a state where the subject 102 is present (S201); and measurement information obtained through measurement that has been performed under measurement control performed by the second measurement control unit 1201 (the measurement control unit 105) in a state where the subject 102 is not present (S1301). The ratio calculation unit 1202 calculates the ratio r using an expression (6) below.

[Math. 6]

$$r = \frac{\sum_i d_i}{a} \tag{6}$$

In the expression (6), the denominator on the right side denotes the measurement information obtained through measurement performed in step S1301 in a state where the subject 102 is not present. The numerator on the right side denotes the pieces of measurement information obtained through measurement that has been performed a plurality of times in step S201 in a state where the subject 102 is present.

Variance Estimation Processing using Measurement Information: S1303

Next, in step S1303, the variance estimation unit 1203 estimates the variance of the energy of radiation using measurement information. In this processing, the variance of the energy distribution of radiation is estimated as a characteristic of the radiation detected by the radiation detecting unit 104, using the pieces of measurement information obtained through measurement that has been performed a plurality of times in step S201 in a state where the subject 102 is present, and the measurement information obtained through measurement that has been performed in step S1031 in a state where the subject 102 is not present. The present embodiment illustrates processing in which the ratio r of the pieces of measurement information obtained through the expression (6) is used in the estimation of the variance of the energy distribution of radiation, presuming the constituent material of the subject 102 to be a certain material. The ratio r of measurement information can be rewritten as shown in an expression (7).

[Math. 7]

$$r = \frac{\int \tilde{s}(E)EdE}{\int s_{in}(E)EdE}, \tilde{s}(E) = s_{in}(E)\exp\left(-\int \mu(E,L)dL\right) \quad (7)$$

Here, μ denotes an attenuation coefficient, and is a function of energy and a position L. The integral with respect to the position L can be calculated on a line segment that connects the radiation generating unit 101 and the measurement element of the radiation detecting unit 104. In the equation (7), the energy distribution (the probability density function) of radiation s(E) can be rewritten as shown in an expression (8).

[Math. 8]

$$s(E) = \frac{\tilde{s}(E)}{\int \tilde{s}(E)dE} \quad (8)$$

In the present embodiment, it is assumed that the constituent material of the subject 102 is polymethyl methacrylate (PMMA), the attenuation coefficient thereof is $\mu_1$, and the length (the thickness) of the subject 102 is $L_1$. That is to say, an approximate expression (9) can be obtained.

[Math. 9]

$$\int \mu(E,L)dL \approx \mu_1(E)L_1 \quad (9)$$

If the approximate expression (9) is obtained, the ratio r of the pieces of measurement information in the expression (7) can be rewritten as shown in an expression (10) below.

[Math. 10]

$$r = \frac{\int s_{in}(E)\exp(-\mu_1(E)L_1)EdE}{\int s_{in}(E)EdE} \quad (10)$$

Also, the expression (8) showing the energy distribution (the probability density function) of radiation can be rewritten as shown in an equation (11) below.

[Math. 11]

$$s(E) = \frac{s_{in}(E)\exp(-\mu_1(E)L_1)}{\int s_{in}(E)\exp(-\mu_1(E)L_1)dE} \quad (11)$$

The energy distribution (the probability density function) $s_{in}(E)$ of radiation that has not passed the subject 102 can be measured using a spectrometer in a state where the subject is not present, and the attenuation coefficient $\mu_1$ of PMMA can also be measured separately through an experiment. The ratio r regarding measurement information and the energy distribution (the probability density function) s(E) of radiation that has passed through the subject can be calculated if the length (the thickness) $L_1$ is determined. Also, if the energy distribution (the probability density function) s(E) of radiation that has passed through the subject 102 is determined, the variance $\sigma_s^2$ can also be calculated. Therefore, by calculating in advance the ratio r regarding measurement information and the variance $\sigma_s^2$ for various lengths (thicknesses) $L_1$, it is possible to obtain the correspondence relationship between the ratio r regarding measurement information and the variance $\sigma_s^2$, and thus it is possible to obtain the variance $\sigma_s^2$ from the value of the ratio r regarding measurement information.

Although the above-described method is employed in the present embodiment, the variance $\sigma_s^2$ may be calculated without obtaining the correspondence relationship between the ratio r regarding measurement information and the variance $\sigma_s^2$ in advance, and may be calculated by analyzing the equation (10) with respect to the length (the thickness) $L_1$ through a Newton-Raphson method, for example, thereafter obtaining the energy distribution (the probability density function) s(E) of radiation using the expression (11), and employing the expression (3) based on s(E) thus obtained.

In a case of a CT apparatus, it is possible to estimate the variance $\sigma_s^2$ without obtaining the value of the ratio r regarding measurement information. When imaging is to be performed using a CT apparatus, first, images of the subject are captured at various projection angles. Next, using pieces of measurement information obtained through measurement that has been performed a plurality of times in a state where the subject is present, and measurement information obtained through measurement performed in a state where the subject is not present, a statistical image reconstruction method (the MLEM method) is performed to obtain a three-dimensional attenuation coefficient distribution regarding the subject. Thereafter, the three-dimensional distribution of the constituent materials of the subject is estimated based on the value of the attenuation coefficient. Finally, by performing a projection calculation, which is part of the statistical image reconstruction method (the MLEM method), the energy distribution (the probability density function) s(E) of radiation is obtained, and the variance $\sigma_s^2$ can be calculated using the expression (3), based on s(E) thus obtained.

The variance estimation unit 1203 can calculate the variance $\sigma_s^2$ of the energy of radiation by executing variance estimation processing using measurement information. Thereafter, as in the first embodiment the average energy correction unit 109 corrects the average energy $E_{stat}$ in step S206, using the variance $\sigma_s^2$ of the energy of radiation, which has been estimated through variance estimation processing (S1303) using measurement information. Specifically, the average energy correction unit 109 obtains the corrected average energy $E'_{stat}$ as shown in (4).

Thus, average energy correction processing is complete. Also, if necessary, it is possible to display the average energy, the variance of the energy distribution of radiation, the true average energy (the corrected average energy), and so on, using the display unit 110, to check the effect of correction, or use them to make a diagnosis.

With reference to FIGS. 14 and 15, the following describes an example in which the average energy is corrected through the average energy correction processing described in the present embodiment, in a case where imaging is performed based on the arrangement of subjects shown in FIG. 5. The arrangement of the subjects and conditions for the numerical calculation are the same as those in the first embodiment. Therefore, the following only shows the results of average energy correction processing.

FIG. 14 shows an image of the average energy $E'_{stat}$ that has been corrected through the processing procedures according to the present embodiment. The scale shown above the image in FIG. 14 indicates a correspondence relationship between gray levels in the image and energy levels. This image is blacker overall than the image of the uncorrected average energy $E_{stat}$ (FIG. 8), which indicates that the values of the corrected average energy $E'_{stat}$ are close to the values of the true average energy $\mu_s$. In order to more easily make a comparison, FIG. 15 shows an image of relative errors between the corrected average energy $E'_{stat}$ and the true average energy $\mu_s$. The scale shown above the image in FIG. 15 indicates a correspondence relationship between gray levels in the image and relative errors of the energy levels. The density of the image decreases (the image becomes whiter) as the relative errors increase, and the density of the image increases (the image becomes blacker) as the relative errors decrease.

When compared with the image showing relative errors between the uncorrected average energy $E_{stat}$ and the true average energy $\mu_s$ (FIG. 10), the image showing relative errors in the corrected average energy $E'_{stat}$ is blacker overall than the image showing relative errors in the uncorrected average energy $E_{stat}$, which indicates that the relative errors have been reduced. With the present embodiment, it is possible to calculate an average energy with high accuracy, through average energy correction processing. As a result, it is possible to accurately distinguish between internal structures that cannot be distinguished from each other if integrated values of energy are used.

Third Embodiment

Figure 16:
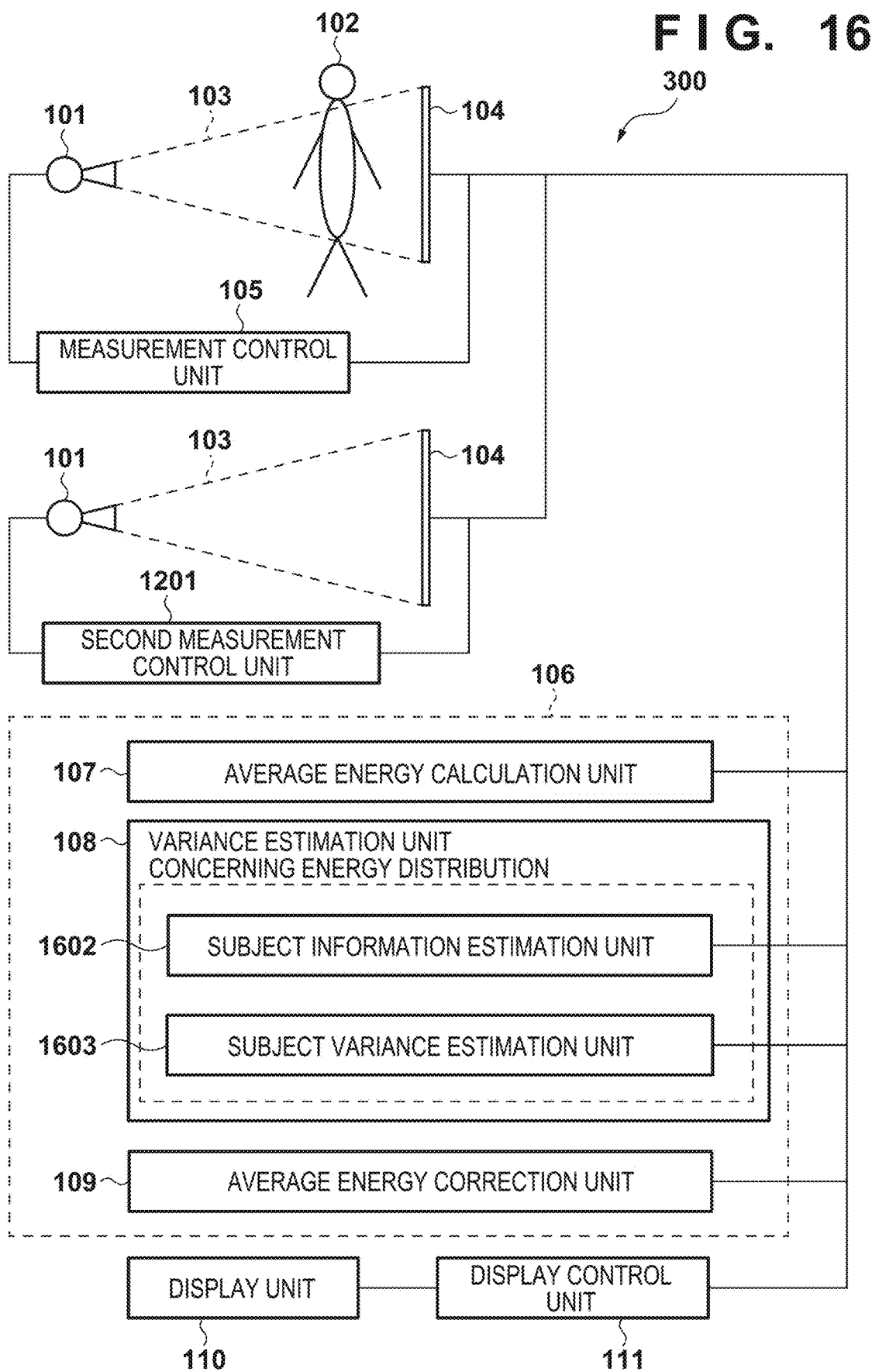
FIG. 16 is a schematic diagram showing a configuration of a radiation imaging apparatus according to a third embodiment.
Figure 17:
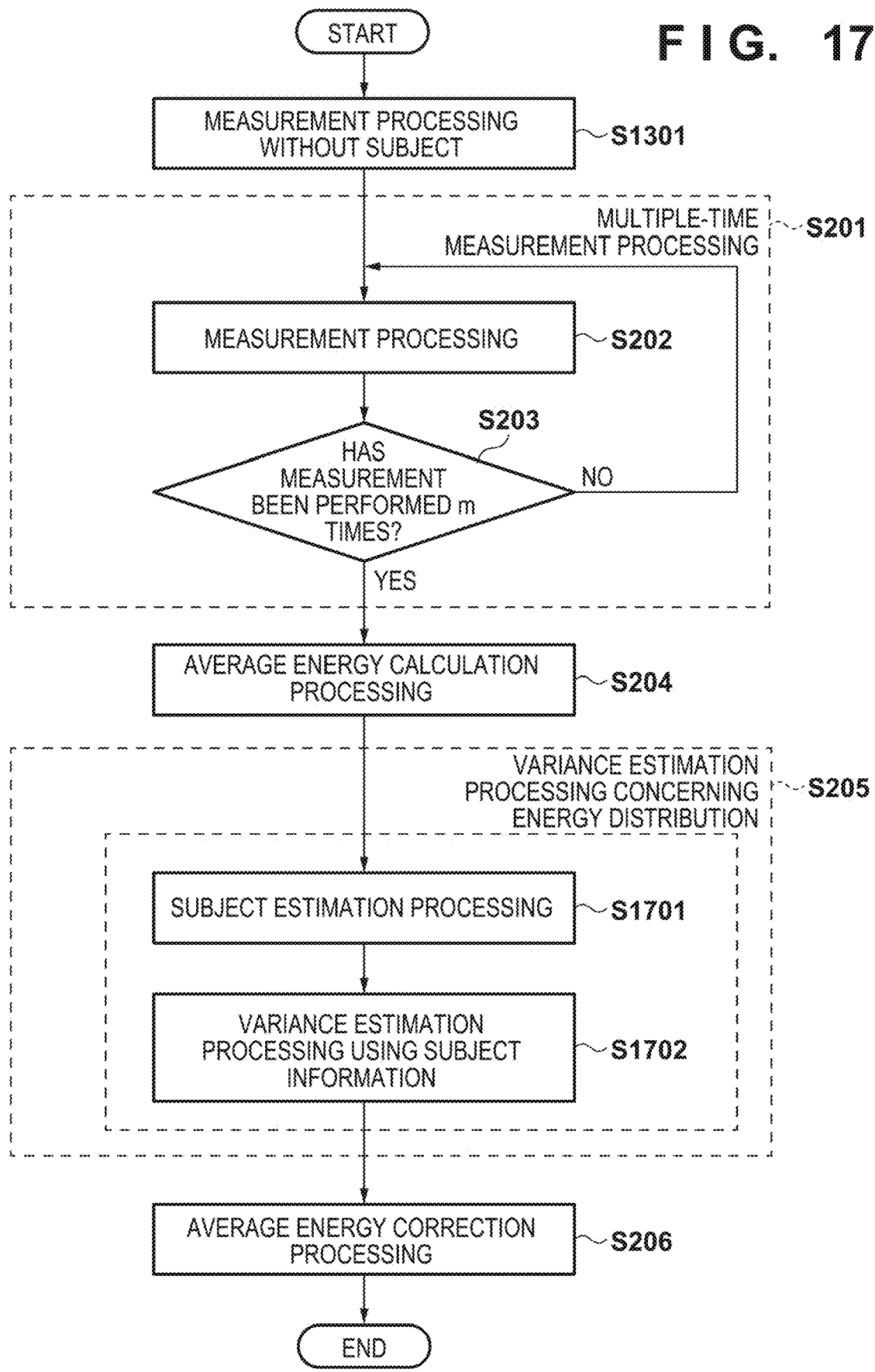
FIG. 17 is a flowchart for average energy correction processing according to the third embodiment.

The following specifically describes a third embodiment of the present invention with reference to the accompanying drawings. FIG. 16 is a diagram showing a configuration of a radiation imaging apparatus 300 according to the third embodiment, and FIG. 17 is a flowchart for an average energy correction processing. With reference to these figures, the following describes the configuration of the radiation imaging apparatus 300 and processing procedures according to the third embodiment. In order to avoid duplicative descriptions, the following describe parts that differ from the configuration according to the second embodiment. Parts that are assigned the same reference numerals perform the same functions and the same processing.

The variance estimation unit 108 concerning energy distribution, included in the image processing unit 106, includes a subject information estimation unit 1602 that estimates subject information, and a subject variance estimation unit 1603 that uses subject information, as functional elements. The functions of the subject information estimation unit 1602 and the subject variance estimation unit 1603 are achieved using a CPU, a GPU, and programs that are read out from a memory, for example (not shown). That is to say, processing that is performed by the subject information estimation unit 1602 and the subject variance estimation unit 1603 is realized by a computer executing functions of programs corresponding to the functional elements. The image processing unit 106 may be formed using an integrated circuit or the like if similar functions can be achieved, and is not limited to any mode.

Next, procedures for average energy correction processing that is performed by the radiation imaging apparatus 300 according to the third embodiment will be described with reference to the flowchart shown in FIG. 17. The following describes processing that differs from the flowchart in FIG. 2 or FIG. 13, while duplicative descriptions are omitted. First, in step S1301, measurement information is obtained through measurement that is performed in a state where the subject is not present, and, in step S201, pieces of measurement information are obtained through measurement that is performed a plurality of times in a state where the subject is present. Thereafter, in step S204, the average energy of radiation is obtained.

Subject Estimation Processing: S1701

Next, in step S1701, the subject information estimation unit 1602 estimates the thickness of the constituent material based on: pieces of measurement information obtained through measurement of the energy of radiation that has been performed a plurality of times in a state where the subject is present; measurement information obtained through measurement of the energy of radiation that has been performed in a state where the subject is not present; and the constituent material of the subject. The subject information estimation unit 1602 estimates the thickness of the constituent material, using the pieces of measurement information obtained in step S201 through measurement of the energy of radiation that has been performed in a state where the subject 102 is present, the measurement information obtained in step S1301 through measurement that has been performed in a state where the subject 102 is not present, and the average energy obtained in step S204, presuming the constituent material of the subject 102 to be a certain material.

The present embodiment describes an example in which it is presumed that a soft tissue and a bone are the constituent materials of the subject. The materials constituting the subject can be approximated as shown in an expression (12).

[Math. 12]

$$\int \mu(E,L)dL \approx \mu_1(E)L_1 + \mu_2(E)L_2 \quad (12)$$

Here, $\mu_1$ denotes the attenuation coefficient of a soft tissue, and $L_1$ denotes the length (the thickness) of the soft tissue. $\mu_2$ denotes the attenuation coefficient of a constituent material that is harder than the soft tissue, such as a bone, and $L_2$ denotes the length (the thickness) of the bone. The expression (7), which indicates the ratio r regarding measurement information, can be rewritten as shown in an expression (13), and the expression (8), which indicates the energy distribution (the probability density function) s(E) of radiation, can be written as shown in an expression (14).

[Math. 13]

$$r = \frac{\int s_{in}(E)\exp(-\mu_1(E)L_1 - \mu_2(E)L_2)EdE}{\int s_{in}(E)EdE} \quad (13)$$

[Math. 14]

$$s(E) = \frac{s_{in}(E)\exp(-\mu_1(E)L_1 - \mu_2(E)L_2)}{\int s_{in}(E)\exp(-\mu_1(E)L_1 - \mu_2(E)L_2)dE} \quad (14)$$

The energy distribution (the probability density function) $s_{in}(E)$ of radiation that has not passed the subject 102 can be measured using a spectrometer in a state where the subject is not present, and the attenuation coefficients $\mu_1$ and $\mu_2$ can also be measured separately through an experiment. It is also possible to obtain the ratio r regarding measurement information through the expression (6), using the pieces of measurement information obtained through measurement that has been performed a plurality of times in a state where the subject 102 is present and measurement information that has been measured in a state where the subject 102 is not present.

Also, in this step, the variance $\sigma_s^2$ is ignored, and an approximation is made to regard the uncorrected average energy $E_{stat}$ as being equal to the true average energy $\mu_s$. The energy distribution (probability density function) s(E) of radiation in the expression (14) is substituted into the expression (3), and the uncorrected average energy is obtained through the equation (15).

[Math. 15]

$$E_{stat} = \frac{\int s_{in}(E)\exp(-\mu_1(E)L_1 - \mu_2(E)L_2)E dE}{\int s_{in}(E)\exp(-\mu_1(E)L_1 - \mu_2(E)L_2)dE} \quad (15)$$

The uncorrected average energy $E_{stat}$ has been obtained in step S204, and therefore unknown parameters in the expressions (13) and (15) are the lengths (the thicknesses) $L_1$ and $L_2$ of the constituent materials of the subject 102. The lengths (the thicknesses) $L_1$ and $L_2$ of the constituent materials of the subject 102 can be obtained by solving the nonlinear simultaneous equations. In the present embodiment, the Newton-Raphson method is used as a method for numerically analyzing the nonlinear simultaneous equations. Through the above-described processing, the subject information estimation unit 1602 can obtain the lengths (the thicknesses) $L_1$ and $L_2$ regarding the subject.

In the present embodiment, an approximation is made to regard the uncorrected average energy $E_{stat}$ is equal to the true average energy μs. However, the present invention is not limited to this example. Alternatively, it is possible to perform the processing by correcting the average energy $E_{stat}$ in advance through the methods described in the first embodiment and the second embodiment to obtain the corrected average energy $E'_{stat}$, and making an approximation to regard $E'_{stat}$ thus obtained as being equal to $\mu_s$.

Variance Estimation Processing using Subject Information: S1702

Next, in step S1702, the subject variance estimation unit 1603 obtains the energy distribution of radiation in a state where the subject is present, based on: the attenuation coefficient of the constituent materials of the subject; information regarding the thicknesses of the constituent materials; and the energy distribution of radiation in a state where the subject is not present, and estimates the variance $\sigma_s^2$ of the energy distribution s(E) of the radiation in a state where the subject is present, based on the energy distribution of the radiation thus obtained. The subject variance estimation unit 1603 estimates, as a characteristic of the radiation detected by the radiation detecting unit 104, the variance of the energy distribution of the radiation, using information regarding the lengths (the thicknesses) of the constituent materials of the subject 102 obtained in step S1701. Specifically, the subject variance estimation unit 1603 substitutes the energy distribution (the probability density function) s(E) of the radiation shown in the expression (14) into the expression (3) to obtain the variance $\sigma_s^2$ of the energy distribution s(E) of the radiation in a state where the subject is present.

In step S1702, the variance $\sigma_s^2$ of the energy distribution s(E) of the radiation has been estimated. Therefore, by performing average energy correction processing as in step S206 according to the first embodiment, the average energy correction unit 109 corrects the average energy $E_{stat}$ obtained in step S204, using the variance $\sigma_s^2$ obtained through variance estimation processing (S1702) concerning energy distribution.

Thus, average energy correction processing is complete. Also, if necessary, it is possible to display the average energy, the variance of the energy distribution of radiation, the true average energy (the corrected average energy), and so on, using the display unit 110, to check the effect of correction, or use them to make a diagnosis.

Figure 18:
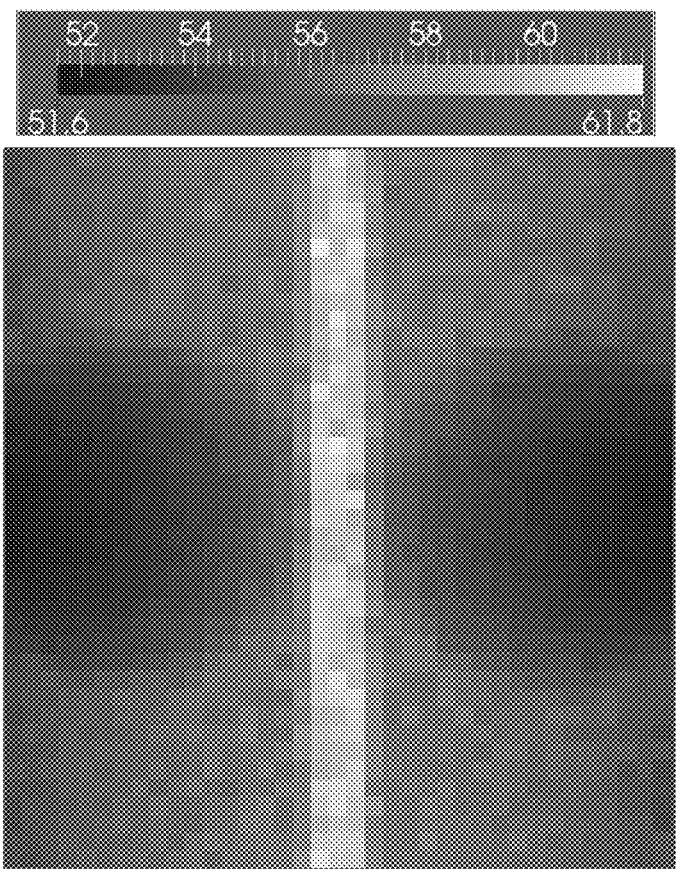
FIG. 18 is a diagram showing an example of a corrected average energy image.
Figure 19:
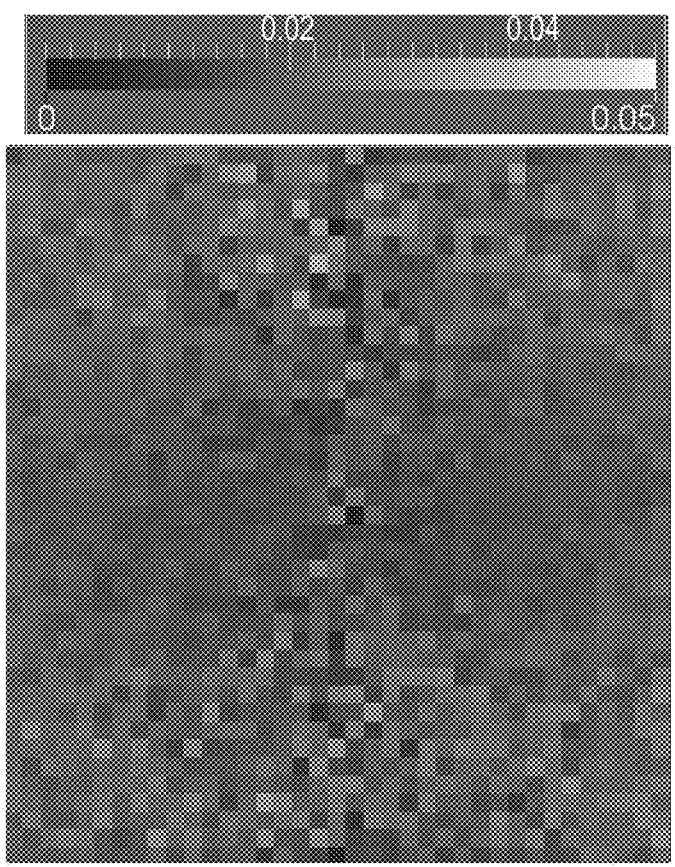
FIG. 19 is a diagram showing an example of a relative error image regarding corrected average energy.

With reference to FIGS. 18 and 19, the following describes an example in which the average energy is corrected through the average energy correction processing described in the present embodiment, in a case where imaging is performed based on the arrangement of subjects shown in FIG. 5. The arrangement of the subjects and conditions for the numerical calculation are almost the same as those in the first embodiment. Therefore, the following only shows the results of average energy correction processing.

FIG. 18 shows an image of the average energy $E'_{stat}$ that has been corrected through the processing procedures according to the present embodiment. The scale shown above the image in FIG. 18 indicates a correspondence relationship between gray levels in the image and energy levels. This image is blacker overall than the image of the uncorrected average energy $E_{stat}$ (FIG. 8), which indicates that the values of the corrected average energy $E'_{stat}$ are close to the values of the true average energy $\mu_s$. In order to more easily make a comparison, FIG. 19 shows an image of relative errors between the corrected average energy $E'_{stat}$ and the true average energy $\mu_s$. The scale shown above the image in FIG. 19 indicates a correspondence relationship between gray levels in the image and relative errors of the energy levels. The density of the image decreases (the image becomes whiter) as the relative errors increase, and the density of the image increases (the image becomes blacker) as the relative errors decrease.

When compared with the image showing relative errors between the uncorrected average energy $E_{stat}$ and the true average energy $\mu_s$ (FIG. 10), the image showing relative errors in the corrected average energy $E'_{stat}$ is blacker overall than the image showing relative errors in the uncorrected average energy $E_{stat}$, which indicates that the relative errors have been reduced. With the present embodiment, it is possible to calculate an average energy with high accuracy, through average energy correction processing. As a result, it is possible to accurately distinguish between internal structures that cannot be distinguished from each other if integrated values of energy are used.

According to an aspect of the present invention, it is possible to reduce an error that occurs due to the characteristics of radiation, through correction, and obtain average energy with high accuracy.

Other Embodiments

Embodiment(s) of the present invention can also be realized by a computer of a system or apparatus that reads out and executes computer executable instructions (e.g., one or more programs) recorded on a storage medium (which may also be referred to more fully as anon-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus comprising:
a detecting unit configured to obtain measurement information that is based on a result of detection of radiation with which a subject has been irradiated, wherein the detecting unit has a plurality of detecting elements that are two-dimensionally arranged;
a central processing unit (CPU); and
at least one memory, the CPU and the at least one memory cooperating to provide:
an obtaining unit configured to obtain average energy of the radiation based on a first-order moment about an origin for the measurement information and a second-order central moment for the measurement information obtained through measurement of the radiation that has been performed a plurality of times;
an estimation unit configured to estimate a variance of energy distribution of the radiation as a characteristic of the radiation; and
a correction unit configured to correct the average energy based on the variance of energy distribution of the radiation with which the subject has been irradiated.

2. The radiation imaging apparatus according to claim 1, wherein the estimation unit uses the variance of the energy distribution of the radiation that has not passed through the subject, as the variance of the energy distribution.

3. The radiation imaging apparatus according to claim 1, wherein the CPU and the at least one memory further cooperate to provide:
a measurement control unit that causes a radiation generating unit configured to emit the radiation, and the detecting unit, to operate in conjunction with each other to control measurement of the energy of the radiation, and
wherein the measurement control unit controls measurement of the energy of the radiation that has been performed a plurality of times, in a state where the subject is present between the radiation generating unit and the detecting unit.

4. The radiation imaging apparatus according to claim 3, wherein the measurement control unit controls measurement of the energy of the radiation, in a state where the subject is not present between the radiation generating unit and the detecting unit.

5. The radiation imaging apparatus according to claim 1, wherein the CPU and the at least one memory further cooperate to provide a ratio calculation unit configured to obtain a ratio regarding measurement information based on:
pieces of measurement information obtained through measurement of the energy of the radiation that has been performed a plurality of times in a state where the subject is present; and
measurement information obtained through measurement of the energy of the radiation that has been performed in a state where the subject is not present, and
wherein the estimation unit obtains the variance of the energy distribution based on the ratio regarding measurement information.

6. The radiation imaging apparatus according to claim 5, wherein the ratio calculation unit obtains the ratio regarding measurement information based on information regarding a material that constitutes the subject, and the energy distribution of the radiation in a state where the subject is not present, and
the estimation unit obtains the variance of the energy distribution based on the ratio regarding measurement information.

7. The radiation imaging apparatus according to claim 5, wherein the estimation unit includes a subject estimation unit configured to estimate a thickness of a constituent material of the subject, and
the subject estimation unit estimates the thickness of the constituent material based on:
pieces of measurement information obtained through measurement of the energy of radiation that has been performed a plurality of times in a state where the subject is present; measurement information obtained through measurement of the energy of the radiation that has been performed in a state where the subject is not present; and
the constituent material of the subject.

8. The radiation imaging apparatus according to claim 7, wherein the estimation unit includes a subject variance estimation unit configured to obtain the energy distribution of the radiation in a state where the subject is present, based on information regarding the subject, and
the subject variance estimation unit obtains the energy distribution of the radiation in a state where the subject is present, based on:
an attenuation coefficient of the constituent material; information regarding the thickness of the constituent material; and
the energy distribution of the radiation in a state where the subject is not present.

9. The radiation imaging apparatus according to claim 8, wherein the subject variance estimation unit estimates the variance of the energy distribution of the radiation in a state where the subject is present, based on the obtained energy distribution of the radiation.

10. The radiation imaging apparatus according to claim 1, wherein the CPU and the at least one memory further cooperate to provide a display control unit configured to display, on a display unit, an image indicating a distribution of the average energy corrected by the correction unit, and an image indicating a distribution of uncorrected average energy.

11. The radiation imaging apparatus according to claim 1, wherein the obtaining unit obtains the average energy of the radiation based on pieces of measurement information obtained through measurement of the radiation that has been performed a plurality of times.

12. The radiation imaging apparatus according to claim 1, wherein the correction unit corrects the average energy based on a characteristic of the radiation with which the subject has been irradiated.

13. A radiation imaging method for a radiation imaging apparatus that includes a detecting unit that obtains measurement information that is based on a result of detection of radiation with which a subject has been irradiated, wherein the detecting unit has a plurality of detecting elements that are two-dimensionally arranged, the radiation imaging method comprising:

obtaining an average energy of the radiation based on a first-order moment about an origin for the measurement information and a second-order central moment for the measurement information obtained through measurement of the radiation that has been performed a plurality of times;

estimating a variance of energy distribution of the radiation as a characteristic of the radiation; and correcting the average energy based on the variance of energy distribution of the radiation with which the subject has been irradiated.

14. A computer-readable storage medium storing a program that causes a computer to execute a radiation imaging method for a radiation imaging apparatus that includes a detecting unit that obtains measurement information that is based on a result of detection of radiation with which a subject has been irradiated, wherein the detecting unit has a plurality of detecting elements that are two-dimensionally arranged, the radiation imaging method comprising:

obtaining an average energy of the radiation based on a first-order moment about an origin for the measurement information and a second-order central moment for the measurement information obtained through measurement of the radiation that has been performed a plurality of times;

an estimation step of estimating a variance of energy distribution of the radiation as a characteristic of the radiation; and correcting the average energy based on the variance of energy distribution of the radiation with which the subject has been irradiated.

* * * * *